(12) United States Patent
Nelson (10) Patent No.: US 9,468,213 B2
(45) Date of Patent: Oct. 18, 2016

(54) HERBICIDE FORMULATION

(71) Applicant: Alan Frederick Nelson, Browns-Summit, NC (US)

(72) Inventor: Alan Frederick Nelson, Browns-Summit, NC (US)

(73) Assignee: Syngenta Crop Protection LLC, Greensboro, NC (US)

( * ) Notice: Subject to any disclaimer, the term of this patent is extended or adjusted under 35 U.S.C. 154(b) by 64 days.

(21) Appl. No.: 14/243,474

(22) Filed: Apr. 2, 2014

(65) Prior Publication Data

US 2014/0213450 A1    Jul. 31, 2014

Related U.S. Application Data

(63) Continuation of application No. 12/918,732, filed as application No. PCT/EP2009/000979 on Feb. 12, 2009, now abandoned.

(60) Provisional application No. 61/029,996, filed on Feb. 20, 2008.

(51) Int. Cl.
| | | |
|---|---|---|
| *A01N 43/56* | (2006.01) | |
| *A01N 43/80* | (2006.01) | |
| *A01N 37/18* | (2006.01) | |
| *A01N 57/20* | (2006.01) | |
| *A01N 37/22* | (2006.01) | |
| *A01N 37/26* | (2006.01) | |
| *A01N 41/10* | (2006.01) | |
| *A01N 43/10* | (2006.01) | |

(52) U.S. Cl.
CPC ............... *A01N 57/20* (2013.01); *A01N 37/18* (2013.01); *A01N 37/22* (2013.01); *A01N 37/26* (2013.01); *A01N 41/10* (2013.01); *A01N 43/10* (2013.01); *A01N 43/56* (2013.01); *A01N 43/80* (2013.01)

(58) Field of Classification Search
None
See application file for complete search history.

(56) References Cited

U.S. PATENT DOCUMENTS

| 5,538,936 A | 7/1996 | Hermansky |
| 5,912,207 A | 6/1999 | Scher et al. |
| 7,951,390 B2 | 5/2011 | Jadhav et al. |
| 2006/0211578 A1 | 9/2006 | Cornes et al. |
| 2007/0010401 A1 | 1/2007 | Noon et al. |

FOREIGN PATENT DOCUMENTS

| WO | 9734486 | 9/1997 |
| WO | 2004080178 | 9/2004 |
| WO | 2004112481 | 12/2004 |
| WO | WO2014003350 | 1/2014 |

OTHER PUBLICATIONS

The Merck Index, 14th Edition, O'Neill, ed. 2006, entry for toluenesulfonic acid.

*Primary Examiner* — Sue Liu
*Assistant Examiner* — Thor Nielsen
(74) *Attorney, Agent, or Firm* — James Cueva (57) ABSTRACT

The present invention relates, inter alia, to a novel herbicide formulation comprising:— (a) an aqueous phase; (b) an HPPD inhibitor in suspension in the aqueous phase; (c) an encapsulated chloroacetamide or an isoxazoline herbicide in suspension in the aqueous phase; (d) glyphosate and/or glufosinate or an agrochemically acceptable salt thereof, in solution in the aqueous phase. The invention further relates to a process for the preparation of an herbicide formulation of the invention and to a process for the control of unwanted vegetation.

18 Claims, 2 Drawing Sheets

HERBICIDE FORMULATION

This application is a continuation U.S. application Ser. No. 12/918,732, filed Aug. 20, 2010 which is a 371 of International Application No. PCT/EP2009/000979 filed Feb. 12, 2009, which claims priority to U.S. 61/029,996 filed Feb. 20, 2008, the contents of which is incorporated herein by reference.

BRIEF DESCRIPTION OF THE DRAWINGS

A full and enabling disclosure of the present invention, including the best mode thereof directed to one of ordinary skill in the art, is set forth in the specification, which refers to the appended drawings, in which.

Repeat use of reference characters in the present specification and drawings is intended to represent same or analogous features or elements of the invention.

DESCRIPTION

The present invention relates, inter alia, to a novel herbicide formulation comprising a 4-hydroxyphenylpyruvate dioxygenase (HPPD) inhibitor, a chloroacetamide herbicide or an isoxazoline herbicide and glyphosate and/or glufosinate. The invention further relates to a process for the preparation of an herbicide formulation of the invention and to a process for the control of unwanted vegetation.

The protection of crops from weeds and other vegetation that inhibits crop growth is a constantly recurring problem in agriculture. To help combat this problem, researchers in the field of synthetic chemistry have produced an extensive variety of chemicals and chemical formulations effective in the control of such unwanted growth. Chemical herbicides of many types are disclosed in the literature, for example The Pesticide Manual 14$^{th}$ edition (2006), published by the British Crop Protection Council.

Agricultural pesticide manufacturers have identified the need for broad-spectrum, long-acting pesticidal products. Single active ingredient formulations rarely meet such requirements, and thus combination products, perhaps containing up to four complementary biologically active ingredients, have been developed. For example, WO 2004/112481 teaches a method for the season-long control of unwanted vegetation, said method comprising a single application of an herbicide combination comprising (i) an HPPD inhibitor, (ii) glyphosate and (iii) a chloroacetamide. These pesticidal components can, however, experience adverse chemical and/or physical stability issues when they are combined. For example, the HPPD inhibitor can migrate into the water immiscible chloroacetamide and consequently degrade rapidly. Furthermore, the addition of an ionic soluble liquid (SL), such as glyphosate solution, to a suspension concentrate (SC) can cause the suspended components to fail. Accordingly, pesticide components such as these are typically combined shortly before application.

There remains a need, therefore, to provide a herbicide formulation which allows these types of pesticides to be combined in a physically and chemically stable manner.

Thus according to the present invention there is provided an herbicide formulation comprising:—
(a) an aqueous phase;
(b) an HPPD inhibitor in suspension in the aqueous phase;
(c) an encapsulated chloroacetamide or an isoxazoline herbicide in suspension in the aqueous phase;
(d) glyphosate and/or glufosinate or an agrochemically acceptable salt thereof, in solution in the aqueous phase.

The novel formulation of the present invention is particularly advantageous in that it allows the provision of a stable, user friendly "pre-mix" concentrate.

Accordingly, the present invention further provides an herbicide formulation concentrate comprising:—
(a) an aqueous phase;
(b) 10-600 g/l HPPD inhibitor in suspension in the aqueous phase;
(c) 10-6000 g/l chloroacetamide herbicide or an isoxazoline herbicide which is encapsulated and in suspension in the aqueous phase;
(d) 10-3000 g/l glyphosate and/or glufosinate or an agrochemically acceptable salt thereof, in solution in the aqueous phase; and
(e) a structuring agent.

In a preferred embodiment the concentration on the HPPD inhibitor is from about 10 to about 300 g/l, more preferably from about 10 to about 50 g/l.

In a preferred embodiment the concentration of the chloroacetamide or the isoxazoline herbicide is, independently, from about 100 to about 1000 g/l, more preferably from about 100 to about 500 g/l.

In a preferred embodiment the concentration of the glyphosate and/or glufosinate is independently of one another from about 100 to about 1000 g/l, more preferably from about 100 to about 500 g/l.

The structuring agent is provided in the concentrate formulation in order to maintain the physical stability. Suitable structuring agents are well known to the skilled person, for example xanthan gum. The structuring agent is typically present at from about 1 to 10 g/l.

The individual pesticide compounds comprised by the formulation of the invention are independently known in the art. Suitably the HPPD inhibitor is selected from the group consisting of isoxazoles, triketones, pyrazoles, benzobicyclon and ketospiradox.

Suitably, the isoxazole is a compound of formula (IA)

wherein R is hydrogen or —CO$_2$R$^3$;
R$^1$ is C$_{1-4}$ alkyl or C$_{3-6}$ cycloalkyl optionally substituted by C$_{1-6}$ alkyl;
R$^2$ is independently selected from halogen, nitro, cyano, C$_{1-4}$ alkyl, C$_{1-4}$ haloalkyl, C$_{1-6}$ alkoxy, C$_{1-4}$ haloalkoxy, —(CR$^4$R$^5$)$_c$S(O)$_b$R$^6$, —S(O)$_b$R$^6$, —OSO$_2$R$^6$ and —N(R$^7$)SO$_2$R$^6$;
or two groups R$^2$, on adjacent carbon atoms of the phenyl ring may, together with the carbon atoms to which they are attached, form a 5- or 6-membered saturated or unsaturated heterocyclic ring containing up to three ring heteroatoms selected from nitrogen, oxygen and sulphur, which ring may be optionally substituted by one or more groups selected from halogen, nitro, C$_{1-4}$ alkyl, C$_{1-4}$ alkoxy, C$_{1-4}$ haloalkyl, C$_{1-4}$ haloalkoxy and —S(O)$_b$R$^6$, it being understood that a sulphur atom, where present in the ring, may be in the form of a group —SO— or —SO$_2$—;

$R^3$ is $C_{1-4}$ alkyl;

$R^4$ and $R^5$ are independently hydrogen or $C_{1-4}$ alkyl;

$R^6$ is $C_{1-4}$ alkyl, or phenyl or benzyl, each of phenyl and benzyl optionally bearing from one or five substituents which may be the same of different selected from the group consisting of halogen, $C_{1-4}$ alkyl, $C_{1-4}$ alkoxy, $C_{1-4}$ haloalkyl, $C_{1-4}$ haloalkoxy, nitro and —S(O)$_b$CH$_3$;

$R^7$ is hydrogen or $C_{1-6}$ alkyl;

a is an integer from one to five;

b is zero, one or two; and c is one or two (where c is two, the groups (CR$^4$R$^5$) may be the same or different).

Suitably R is hydrogen; $R^1$ is cyclopropyl; $R^2$ is halogen (preferably chloro), —S(O)$_b$CH$_3$, or $C_{1-4}$ haloalkyl (preferably trifluoromethyl); and a is two.

Particularly preferred compounds of formula (IA) include 5-cyclopropyl-4-(2-methylsulfonyl-4-trifluoromethyl)benzoylisoxazole (isoxaflutole) and 4-(2-chloro-4-methylsulphonyl)benzoyl-5-cyclopropylisoxazole (isoxachlortole), especially isoxaflutole.

Suitably, the triketone is a compound of formula (IB), (IB)

wherein each $R^8$ independently represents (C$_{1-4}$)alkyl or CO$_2$R$^{11}$;

$R^9$ represents a halogen atom; a straight- or branched-chain alkyl, alkoxy or alkoxyalkyl group containing up to six carbon atoms which is optionally substituted by one or more groups —OR$^{12}$ or one or more halogen atoms; or a group selected from nitro, cyano, —CO$_2$R$^{13}$, —S(O)$_f$R$^{12}$, —O(CH$_2$)$_g$OR$^{12}$, —COR$^{13}$, —NR$^{13}$R$^{14}$, —SO$_2$NR$^{13}$R$^{14}$, —CONR$^{13}$R$^{14}$, —CSNR$^{13}$R$^{14}$ and —OSO$_2$R$^{15}$;

each $R^{10}$ independently represents halo, nitro, cyano, S(O)$_f$R$^{16}$, OS(O)$_f$R$^{16}$, $C_{1-6}$ alkyl, $C_{1-6}$ alkoxy, $C_{1-6}$ haloalkyl, $C_{1-6}$ haloalkoxy, carboxy, $C_{1-6}$ alkylcarbonyloxy, $C_{1-6}$ alkoxycarbonyl, $C_{1-6}$ alkylcarbonyl, amino, $C_{1-6}$ alkylamino, $C_{1-6}$ dialkylamino having independently the stated number of carbon atoms in each alkyl group, $C_{1-6}$ alkylcarbonylamino, $C_{1-6}$ alkoxycarbonylamino, $C_{1-6}$ alkylaminocarbonylamino, $C_{1-6}$ dialkylaminocarbonylamino having independently the stated number of carbon atoms in each alkyl group, $C_{1-6}$ alkoxycarbonyloxy, $C_{1-6}$ alkylaminocarbonyloxy, $C_{1-6}$ dialkylcarbonyloxy, phenylcarbonyl, substituted phenylcarbonyl, phenylcarbonyloxy, substituted phenylcarbonyloxy, phenylcarbonylamino, substituted phenylcarbonylamino, phenoxy or substituted phenoxy;

$R^{11}$ is $C_{1-4}$ alkyl;

$R^{12}$ represents a straight- or branched-chain alkyl group containing up to six carbon atoms which is optionally substituted by one or more halogen atoms;

$R^{13}$ and $R^{14}$ each independently represents a hydrogen atom; or a straight- or branched-chain alkyl group containing up to six carbon atoms which is optionally substituted by one or more halogen atoms;

$R^{15}$ represents a straight- or branched-chain alkyl, alkenyl or alkynyl group containing up to six carbon atoms optionally substituted by one or more halogen atoms; or a cycloalkyl group containing from three to six carbon atoms;

$R^{16}$ represents a straight or branched-chain alkyl group containing up to six carbon atoms;

d is zero or an integer from one to six;

e is zero or an integer from one to four;

f is zero, one or two; and g is one, two or three.

Suitably, $R^9$ is selected from the group consisting of chloro, bromo, nitro, cyano, $C_{1-4}$ alkyl, —CF$_3$, —S(O)$_f$R$^{12}$, —C$_{1-4}$-alkyl-OR$^{12}$; each $R^{10}$ is independently chloro, bromo, nitro, cyano, $C_{1-4}$ alkyl, —CF$_3$, —OR$^{12}$, —OS(O)$_f$R$^{16}$ or —S(O)$_f$R$^{16}$; d is zero and e is one or two.

Preferred compounds of formula (IB) are 2-(2'-nitro-4'-methylsulphonylbenzoyl)-1,3-cyclohexanedione (mesotrione), 2-[2-chloro-4-(methylsulfonyl)benzoyl]-1,3-cyclohexanedione (sulcotrione), 2-[2-chloro-4-(methylsulfonyl)-3-[(2,2,2-trifluoroethoxy)methyl]benzoyl]-1,3-cyclohexanedione (tembotrione), 2-(2'-nitro-4'-methylsulphonyloxybenzoyl)-1,3-cyclohexanedione, 4,4-dimethyl-2-(4-methanesulphonyl-2-nitrobenzoyl)-1,3-cyclohexanedione, 2-(2-chloro-3-ethoxy-4-methanesulphonylbenzoyl)-5-methyl-1,3-cyclohexanedione and 2-(2-chloro-3-ethoxy-4-ethanesulphonylbenzoyl)-5-methyl-1,3-cyclohexanedione; especially preferred are 2-(2'-nitro-4'-methylsulphonylbenzoyl)-1,3-cyclohexanedione and 2-[2-chloro-4-(methylsulfonyl)-3-[(2,2,2-trifluoroethoxy)methyl]benzoyl]-1,3-cyclohexanedione, and most preferred is 2-(2'-nitro-4'-methylsulphonyl benzoyl)-1,3-cyclohexanedione.

Alternatively, the triketone is a compound of formula (IC)

(IC)

wherein V is $C_{1-2}$ alkylene, which may be mono- or poly-substituted by $R^{26}$; or, when $R^{18}$ and $R^{19}$ are other than $C_{2-3}$ alkylene, V may additionally be carbonyl, oxygen or —NR$^{27}$—;

W is CR$^{28}$ or N(O)$_g$;

$R^{17}$, $R^{18}$, $R^{19}$ and $R^{20}$ are independently hydrogen, $C_{1-4}$ alkyl, phenyl, $C_{1-4}$ alkoxy, halogen, hydroxy, cyano, hydroxycarbonyl or $C_{1-4}$ alkoxycarbonyl; or $R^{18}$ and $R^{19}$ together are $C_{2-3}$ alkylene, which may be mono- or poly-substituted by $R^{25}$;

$R^{21}$ is hydrogen, $C_{1-6}$ alkyl, $C_{1-6}$ haloalkyl, $C_{2-6}$ alkenyl, $C_{2-6}$ haloalkenyl, $C_{1-2}$ alkoxycarbonyl- or phenyl-substituted vinyl, $C_{2-6}$ alkynyl, $C_{2-6}$ haloalkynyl, trimethylsilyl-, hydroxy-, $C_{1-6}$ alkoxy-, C alkoxycarbonyl- or phenyl-substituted ethynyl, $C_{3-6}$ allenyl, $C_{3-6}$ cycloalkyl, halo- or $C_{1-3}$ alkoxymethyl-substituted $C_{3-6}$ cycloalkyl, $C_{1-6}$ alkoxy, $C_{3-6}$ alkenyloxy, $C_{3-6}$ alkynyloxy, $C_{1-6}$ haloalkoxy, $C_{3-6}$ haloalkenyloxy, cyano-$C_{1-4}$ alkoxy, $C_{1-4}$ alkoxy-$C_{1-4}$ alkoxy, $C_{1-4}$ alkylthio-$C_{1-4}$ alkoxy, $C_{1-4}$ alkylsulfinyl-$C_{1-4}$ alkoxy, $C_{1-4}$ alkylsulfonyl-$C_{1-4}$ alkoxy, $C_{1-4}$ alkoxycarbonyl-$C_{1-4}$ alkoxy, $C_{1-6}$ alkylthio, $C_{1-6}$ alkylsulfinyl, $C_{1-6}$ alkylsulfonyl, $C_{1-6}$ haloalkylthio, $C_{1-6}$ haloalkylsulfinyl, $C_{1-6}$ haloalkylsulfonyl, $C_{1-4}$ alkoxycarbonyl-$C_{1-4}$ alkylthio, $C_{1-4}$ alkoxycarbonyl-$C_{1-4}$ alkylsulfinyl, $C_{1-4}$ alkoxycarbonyl-$C_{1-4}$ alkylsulfonyl, $C_{1-6}$ alkylamino, di($C_{1-6}$ alkyl)amino, $C_{1-3}$ alkoxy-$C_{1-3}$ alkylamino, $C_{1-3}$ alkoxy-$C_{1-3}$ alkyl-N($C_{1-3}$ alkyl), $C_{1-6}$ alkylaminosulfonyl, di($C_{1-6}$ alkyl)aminosulfonyl, $C_{1-4}$ alkylsulfonyloxy, $C_{1-4}$ haloalkylsulfonyloxy, $C_{1-4}$ alkylsulfonylamino, $C_{1-4}$ alkylsulfonyl-N($C_{1-4}$ alkyl), cyano, carbamoyl, $C_{1-4}$ alkoxycarbonyl, formyl, halogen, rhodano, amino, hydroxy-$C_{1-4}$ alkyl, $C_{1-4}$ alkoxy-$C_{1-4}$ alkyl, $C_{1-4}$ alkylthio-$C_{1-4}$ alkyl, $C_{1-4}$ alkylsulfinyl-$C_{1-4}$ alkyl, $C_{1-4}$ alkylsulfonyl-$C_{1-4}$ alkyl, cyano-$C_{1-4}$ alkyl, $C_{1-6}$ alkyl-carbonyloxy-$C_{1-4}$ alkyl, $C_{1-4}$ alkoxycarbonyl-$C_{1-4}$ alkyl, $C_{1-4}$ alkoxycarbonyloxy-$C_{1-4}$-alkyl, rhodano-$C_{1-4}$ alkyl, phenyl-$C_{1-4}$ alkyl, phenoxy-$C_{1-4}$ alkyl, benzyloxy-$C_{1-4}$ alkyl, benzoyloxy-$C_{1-4}$ alkyl, (2-oxiranyl)-$C_{1-4}$ alkyl, $C_{1-4}$ alkylamino-$C_{1-4}$ alkyl, di($C_{1-4}$ alkyl) amino-$C_{1-4}$ alkyl, $C_{1-12}$ alkylthiocarbonyl-$C_{1-4}$ alkyl or formyl-$C_{1-4}$ alkyl, or benzylthio, benzylsulfinyl, benzylsulfonyl, benzyloxy, benzyl, phenyl, phenoxy, phenylthio, phenylsulfinyl or phenylsulfonyl, wherein the phenyl-containing groups may themselves be substituted by $C_{1-3}$ alkyl, $C_{1-3}$ haloalkyl, $C_{1-3}$ alkoxy, $C_{1-3}$ haloalkoxy, halogen, cyano or by nitro; or $R^{21}$ is a three- to ten-membered monocyclic or fused bicyclic ring system, which may be aromatic, saturated or partially saturated and may contain from 1 to 4 hetero atoms selected from nitrogen, oxygen and sulfur, wherein the ring system is bonded to the group W-containing aromatic ring by way of a $C_{1-4}$ alkylene, $C_{2-4}$ alkenylene or $C_{2-4}$ alkynylene bridge which may be interrupted by oxygen, —N($C_{1-4}$ alkyl)-, sulfur, sulfinyl, sulfonyl or by carbonyl, and each ring system may contain no more than two oxygen atoms and no more than two sulfur atoms, and the ring system may itself be mono-, di- or tri-substituted by $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{1-6}$ alkoxy, $C_{1-6}$ haloalkoxy, $C_{3-6}$-alkenyloxy, $C_{3-6}$ alkynyloxy, hydroxy, mercapto, $C_{1-6}$ alkylthio, $C_{1-6}$ haloalkylthio, $C_{3-6}$ alkenylthio, $C_{3-6}$ haloalkenylthio, $C_{3-6}$ alkynylthio, $C_{1-4}$ alkoxy-$C_{1-3}$ alkylthio, $C_{1-4}$ alkylcarbonyl-$C_{1-3}$ alkylthio, $C_{1-4}$ alkoxycarbonyl-$C_{1-3}$ alkylthio, cyano-$C_{1-3}$ alkylthio, $C_{1-6}$ alkylsulfinyl, $C_{1-6}$ haloalkylsulfinyl, $C_{1-6}$ alkylsulfonyl, $C_{1-6}$ haloalkylsulfonyl, aminosulfonyl, $C_{1-4}$ alkylaminosulfonyl, di($C_{1-4}$ alkyl)aminosulfonyl, di($C_{1-4}$ alkyl)-amino, halogen, cyano, nitro, phenyl and/or by benzylthio, wherein phenyl and benzylthio may themselves be substituted on the phenyl ring by $C_{1-3}$ alkyl, $C_{1-3}$ haloalkyl, $C_{1-3}$ alkoxy, $C_{1-3}$ haloalkoxy, halogen, cyano or by nitro, and wherein substituents on the nitrogen in the heterocyclic ring are other than halogen; or $R^{21}$ is the group -$D_1$-$D_3$ or the group -$D_2$-$D_1$-$D_3$;

$R^{22}$ is hydrogen, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl, $C_{1-6}$ alkoxy, $C_{1-6}$ haloalkoxy, $C_{1-6}$ alkylthio, $C_{1-6}$ alkylsulfinyl, $C_{1-6}$ alkylsulfonyl, $C_{1-6}$ haloalkylthio, $C_{1-6}$ haloalkylsulfinyl, $C_{1-6}$ haloalkylsulfonyl, $C_{1-6}$ alkylsulfonyloxy, hydroxy, mercapto, amino, $C_{1-6}$ alkylamino, di($C_{1-6}$ alkyl)amino, $C_{1-4}$ alkylsulfonylamino, $C_{1-4}$ alkylsulfonyl-N($C_{1-4}$ alkyl)-, $C_{1-6}$ alkylaminosulfonyl, di($C_{1-6}$ alkyl)aminosulfonyl, cyano, halogen, $C_{1-4}$ alkoxy-$C_{1-4}$ alkyl, $C_{1-4}$ alkylthio-$C_{1-4}$ alkyl, $C_{1-4}$ alkylsulfinyl-$C_{1-4}$ alkyl, $C_{1-4}$ alkylsulfonyl-$C_{1-4}$ alkyl, triazolyl, phenyl, phenylthio, phenylsulfinyl, phenylsulfonyl or phenoxy, wherein the phenyl-containing groups may be substituted by $C_{1-3}$ alkyl, $C_{1-3}$ haloalkyl, $C_{1-3}$ alkoxy, $C_{1-3}$ haloalkoxy, halogen, cyano or by nitro;

$R^{23}$ is hydrogen, $C_{1-6}$ alkyl, hydroxy, $C_{1-6}$ alkoxy, $C_{1-6}$ haloalkoxy, $C_{3-6}$ alkenyloxy, $C_{3-6}$ haloalkenyloxy, $C_{3-6}$ alkynyloxy, $C_{1-4}$ alkylcarbonyloxy, $C_{1-4}$ alkylsulfonyloxy, phenylsulfonyloxy, $C_{1-6}$ alkylthio, $C_{1-4}$ alkylsulfinyl, $C_{1-4}$ alkylsulfonyl, $C_{1-4}$ alkylamino, di($C_{1-4}$ alkyl)amino, $C_{1-4}$ alkoxycarbonyl, $C_{1-4}$ haloalkyl, formyl, cyano, halogen, phenyl or phenoxy, wherein the phenyl-containing groups may themselves be substituted by $C_{1-3}$ alkyl, $C_{1-3}$ haloalkyl, $C_{1-3}$ alkoxy, $C_{1-3}$ haloalkoxy, halogen, cyano or by nitro; or $R^{23}$ is a three- to ten-membered monocyclic or, together with $R^{25}$ or $R^{27}$, fused bicyclic ring system, which may contain from 1 to 4 hetero atoms selected from nitrogen, oxygen and sulfur, wherein, when the ring system is not fused, it is bonded to the W-containing aromatic ring, either directly or by way of a $C_{1-4}$ alkylene, $C_{2-4}$ alkenylene or $C_{2-4}$ alkynylene bridge which may be interrupted by oxygen, —N($C_{1-4}$ alkyl)-, sulfur, sulfinyl, sulfonyl or by carbonyl, and the ring system may contain no more than two oxygen atoms and no more than two sulfur atoms, and the ring system may itself be mono-, di- or tri-substituted by $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{1-6}$ alkoxy, $C_{1-6}$ haloalkoxy, $C_{3-6}$-alkenyloxy, $C_{3-6}$ alkynyloxy, $C_{1-6}$ alkylthio, $C_{1-6}$ haloalkylthio, $C_{3-6}$ alkenylthio, $C_{3-6}$-haloalkenylthio, $C_{3-6}$ alkynylthio, $C_{1-4}$ alkoxy-$C_{1-2}$ alkylthio, $C_{1-4}$ alkylcarbonyl-$C_{1-2}$ alkylthio, $C_{1-4}$ alkoxycarbonyl-$C_{1-2}$ alkylthio, cyano-$C_{1-4}$ alkylthio, $C_{1-6}$ alkylsulfinyl, $C_{1-6}$ haloalkylsulfinyl, $C_{1-6}$ alkylsulfonyl, $C_{1-6}$ haloalkylsulfonyl, aminosulfonyl, $C_{1-4}$-alkylaminosulfonyl, di($C_{1-4}$ alkyl)aminosulfonyl, amino, $C_{1-4}$ alkylamino, di($C_{1-4}$ alkyl)amino, halogen, cyano, nitro, phenyl and by/or benzylthio, wherein phenyl and benzylthio may themselves be substituted on the phenyl ring by $C_{1-3}$ alkyl, $C_{1-3}$ haloalkyl, $C_{1-3}$ alkoxy, $C_{1-3}$ haloalkoxy, halogen, cyano or by nitro, and wherein substituents on the nitrogen in the heterocyclic ring are other than halogen;

$R^{24}$ is hydrogen, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl, $C_{1-6}$ alkoxy, $C_{1-6}$ haloalkoxy, $C_{1-6}$ alkylthio, $C_{1-6}$ alkylsulfinyl, $C_{1-6}$ alkylsulfonyl, $C_{1-6}$ haloalkylthio, $C_{1-6}$ haloalkylsulfinyl, $C_{1-6}$ haloalkylsulfonyl, amino, $C_{1-6}$ alkylamino, di($C_{1-6}$ alkyl)amino, $C_{1-4}$ alkylsulfonyl-N($C_{1-4}$ alkyl)-, $C_{1-6}$ alkylaminosulfonyl, di($C_{1-6}$ alkyl)aminosulfonyl, cyano, halogen, $C_{1-4}$ alkoxy-$C_{1-4}$ alkyl, $C_{1-4}$ alkylthio-$C_{1-4}$ alkyl, $C_{1-4}$ alkylsulfinyl-$C_{1-4}$ alkyl, $C_{1-4}$ alkylsulfonyl-$C_{1-4}$ alkyl, phenyl, phenylthio, phenylsulfinyl, phenylsulfonyl or phenoxy, wherein phenyl groups may themselves be substituted by $C_{1-3}$ alkyl, $C_{1-3}$ haloalkyl, $C_{1-3}$ alkoxy, $C_{1-3}$ haloalkoxy, halogen, cyano or by nitro;

$R^{25}$ and $R^{26}$ are each independently hydrogen, $C_{1-4}$ alkyl, phenyl, $C_{1-4}$ alkoxy, halogen, hydroxy, cyano, hydroxycarbonyl or $C_{1-4}$ alkoxycarbonyl;

$R^{27}$ is $C_{1-4}$ alkyl, alkoxycarbonyl or $C_{1-4}$ alkylcarbonyl;

$R^{28}$ is hydrogen, $C_{1-6}$ alkyl, hydroxy, $C_{1-6}$ alkoxy, $C_{1-6}$ haloalkoxy, $C_{3-6}$ alkenyloxy, $C_{3-6}$ haloalkenyloxy, $C_{3-6}$ alkynyloxy, $C_{1-4}$ alkylcarbonyloxy, $C_{1-4}$ alkylsulfonyloxy, phenylsulfonyloxy, $C_{1-6}$ alkylthio, $C_{1-6}$ alkylsulfinyl, $C_{1-6}$ alkylsulfonyl, $C_{1-6}$ alkylamino, di($C_{1-6}$ alkyl)amino, $C_{1-3}$ alkoxy-$C_{1-3}$ alkylamino, $C_{1-3}$ alkoxy-$C_{1-3}$ alkyl-N($C_{1-3}$ alkyl)-, $C_{1-4}$ alkoxycarbonyl, $C_{1-6}$ haloalkyl, formyl, cyano, halogen, phenyl or phenoxy, wherein the phenyl-containing groups may themselves be substituted by $C_{1-3}$ alkyl, $C_{1-3}$ haloalkyl, $C_{1-3}$ alkoxy, $C_{1-3}$ haloalkoxy, halogen, cyano or by nitro;

or $R^{28}$ is a three- to ten-membered monocyclic or, together with $R^{21}$ or $R^{22}$ fused bicyclic ring system, which may be interrupted once or up to three times by heterocyclic substituents selected from oxygen, sulfur, S(O), $SO_2$, N($R^{29}$), carbonyl and C(=NOR$^{30}$), and wherein, when the ring system is not fused, it is bonded to the carbon atom of the substituent W, either directly or by way of a $C_{1-4}$ alkylene, $C_{2-4}$ alkenylene or $C_{2-4}$ alkynylene bridge which may be interrupted by oxygen, —N($C_{1-4}$ alkyl)-, sulfur, sulfinyl or by sulfonyl, and the ring system may contain no more than two oxygen atoms and no more than two sulfur atoms, and the ring system may itself be mono-, di- or tri-substituted by $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{1-6}$ alkoxy, $C_{1-6}$ haloalkoxy, $C_{3-6}$-alkenyloxy, $C_{3-6}$ alkynyloxy, $C_{1-6}$ alkylthio, $C_{1-6}$ haloalkylthio, $C_{3-6}$ alkenylthio, $C_{3-6}$ haloalkenylthio, $C_{3-6}$ alkynylthio, $C_{1-4}$ alkoxy-$C_{1-2}$ alkylthio, $C_{1-4}$ alkylcarbonyl-$C_{1-2}$-alkylthio, $C_{1-4}$ alkoxycarbonyl-$C_{1-2}$ alkylthio, cyano-$C_{1-4}$ alkylthio, $C_{1-6}$ alkylsulfinyl, $C_{1-6}$ haloalkylsulfinyl, $C_{1-6}$ alkylsulfonyl, $C_{1-6}$ haloalkylsulfonyl, aminosulfonyl, $C_{1-4}$ alkylaminosulfonyl, di($C_{1-4}$ alkyl)aminosulfonyl, di($C_{1-4}$ alkyl)amino, halogen, cyano, nitro, phenyl, benzyloxy and/or by benzylthio, and wherein the phenyl-containing groups may themselves be substituted on the phenyl ring by $C_{1-3}$ alkyl, $C_{1-3}$ haloalkyl, $C_{1-3}$ alkoxy, $C_{1-3}$ haloalkoxy, halogen, cyano or by nitro, and wherein substituents on the nitrogen in the heterocyclic ring are other than halogen;

or $R^{28}$ is the group -$D_4$-$D_6$ or the group -$D_5$-$D_4$-$D_6$;

$R^{29}$ is hydrogen, $C_{1-4}$ alkyl, $C_{1-4}$ alkylthio-$C_{1-4}$ alkylcarbonyl, $C_{1-4}$ alkylsulfinyl-$C_{1-4}$ alkylcarbonyl, $C_{1-4}$ alkylsulfonyl-$C_{1-4}$ alkylcarbonyl, $C_{1-4}$ alkoxycarbonyl, $C_{1-4}$ alkylcarbonyl, phenylcarbonyl or phenyl, wherein the phenyl groups may themselves be substituted by $C_{1-4}$ alkyl, $C_{1-4}$ haloalkyl, $C_{1-4}$ alkoxy, $C_{1-4}$ haloalkoxy, $C_{1-4}$ alkylcarbonyl, $C_{1-4}$ alkoxycarbonyl, $C_{1-4}$ alkylamino, di($C_{1-4}$ alkyl)amino, $C_{1-4}$ alkylthio, $C_{1-4}$ alkylsulfinyl, $C_{1-4}$ alkyl-SO$_2$, $C_{1-4}$ alkyl-S(O)$_2$O, $C_{1-4}$ haloalkylthio, $C_{1-4}$ haloalkylsulfinyl, $C_{1-4}$ haloalkyl-SO$_2$, $C_{1-4}$ haloalkyl-S(O)$_2$O, $C_{1-4}$ alkyl-S(O)$_2$NH, $C_{1-4}$ alkyl-S(O)$_2$N($C_{1-4}$ alkyl)-, halogen, nitro or by cyano;

$R^{30}$ is hydrogen, $C_{1-4}$ alkyl, $C_{3-4}$ alkenyl, $C_{3-4}$ alkynyl or benzyl;

h is 0 or 1;

$D_1$ is oxygen, —O(CO)—, —(CO)O—, —O(CO)O—, —N($C_{1-4}$ alkyl)-O—, —O—N($C_{1-4}$ alkyl)-, thio, sulfinyl, sulfonyl, —SO$_2$N($C_{1-4}$ alkyl)-, —N($C_{1-4}$ alkyl)SO$_2$—, —N($C_{1-2}$ alkoxy-$C_{1-2}$ alkyl)SO$_2$— or —N($C_{1-4}$ alkyl)-;

$D_2$ is a $C_{1-6}$ alkylene, $C_{3-6}$ alkenylene or $C_{3-6}$ alkynylene chain, which may be mono- or poly-substituted by halogen or by $D_7$, the unsaturated bonds of the chain not being bonded directly to the substituent $D_1$;

$D_3$ and $D_6$ are each independently of the other a $C_{1-8}$ alkyl, $C_{3-6}$ alkenyl or $C_{3-6}$ alkynyl group, which may be mono- or poly-substituted by halogen, hydroxy, amino, formyl, nitro, cyano, mercapto, carbamoyl, $C_{1-6}$ alkoxy, $C_{1-6}$ alkoxycarbonyl, $C_{2-6}$ alkenyl, $C_{2-6}$ haloalkenyl, $C_{2-6}$ alkynyl, $C_{2-6}$ haloalkynyl, $C_{3-6}$ cycloalkyl, halo-substituted $C_{3-6}$ cycloalkyl, $C_{3-6}$ alkenyloxy, $C_{3-6}$ alkynyloxy, $C_{1-6}$ haloalkoxy, $C_{3-6}$ haloalkenyloxy, cyano-$C_{1-6}$ alkoxy, $C_{1-6}$ alkoxy-$C_{1-6}$ alkoxy, $C_{1-6}$ alkoxy-$C_{1-6}$ alkoxy-$C_{1-6}$ alkoxy, $C_{1-6}$ alkylthio-$C_{1-6}$ alkoxy, $C_{1-6}$ alkylsulfinyl-$C_{1-6}$ alkoxy, $C_{1-6}$ alkylsulfonyl-$C_{1-6}$ alkoxy, $C_{1-6}$ alkoxycarbonyl-$C_{1-6}$ alkoxy, $C_{1-6}$ alkoxycarbonyl, $C_{1-6}$ alkylcarbonyl, $C_{1-6}$ alkylthio, $C_{1-6}$ alkylsulfinyl, $C_{1-6}$ alkylsulfonyl, $C_{1-6}$ haloalkylthio, $C_{1-6}$ haloalkylsulfinyl, $C_{1-6}$ haloalkylsulfonyl, oxiranyl which may itself be substituted by $C_{1-6}$ alkyl, (3-oxetanyl)-oxy which may itself be substituted by $C_{1-6}$ alkyl, benzyloxy, benzylthio, benzylsulfinyl, benzylsulfonyl, $C_{1-6}$ alkylamino, di($C_{1-6}$-alkyl)amino, $C_{1-4}$ alkyl-S(O)$_2$O, di($C_{1-4}$ alkyl)aminosulfonyl, rhodano, phenyl, phenoxy, phenylthio, phenylsulfinyl or by phenylsulfonyl, and wherein the phenyl- or benzyl-containing groups may themselves be substituted by one or more $C_{1-6}$ alkyl, $C_{1-6}$ haloalkyl, $C_{1-6}$ alkoxy, $C_{1-6}$ haloalkoxy, halogen, cyano, hydroxy or nitro groups; or $D_3$ and $D_6$ are each independently of the other phenyl, which may be mono- or poly-substituted by $C_{1-6}$ alkyl, $C_{1-6}$ haloalkyl, $C_{1-6}$ alkoxy, $C_{1-6}$ haloalkoxy, halogen, cyano, hydroxy or by nitro; or $D_3$ and $D_6$ are each independently of the other $C_{3-6}$ cycloalkyl, $C_{1-6}$ alkoxy- or $C_{1-6}$ alkyl-substituted $C_{3-6}$ cycloalkyl, 3-oxetanyl or $C_{1-6}$ alkyl-substituted 3-oxetanyl; or $D_3$ and $D_6$ are each independently of the other a three- to ten-membered monocyclic or fused bicyclic ring system, which may be aromatic, saturated or partially saturated and may contain from 1 to 4 hetero atoms selected from nitrogen, oxygen and sulfur, wherein the ring system is bonded to the substituent $D_1$ or $D_4$ directly or by way of a $C_{1-4}$ alkylene, $C_{2-4}$ alkenylene, $C_{2-4}$ alkynylene, —N($C_{1-4}$ alkyl)-$C_{1-4}$ alkylene, —S(O)—$C_{1-4}$ alkylene or —SO$_2$—$C_{1-4}$ alkylene group, and each ring system may contain no more than two oxygen atoms and no more than two sulfur atoms, and the ring system may itself be mono-, di- or tri-substituted by $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{1-6}$ alkoxy, hydroxy, $C_{1-6}$ haloalkoxy, $C_{3-6}$ alkenyloxy, $C_{3-6}$ alkynyloxy, mercapto, $C_{1-6}$ alkylthio, $C_{1-6}$ haloalkylthio, $C_{3-6}$ alkenylthio, $C_{3-6}$ haloalkenylthio, $C_{3-6}$ alkynylthio, $C_{1-3}$ alkoxy-$C_{1-3}$ alkylthio, $C_{1-4}$ alkylcarbonyl-$C_{1-2}$ alkylthio, $C_{1-4}$ alkoxycarbonyl-$C_{1-2}$ alkylthio, cyano-$C_{1-3}$ alkylthio, $C_{1-6}$ alkylsulfinyl, $C_{1-6}$ haloalkylsulfinyl, $C_{1-6}$ alkylsulfonyl, $C_{1-6}$ haloalkylsulfonyl, aminosulfonyl, $C_{1-2}$ alkylaminosulfonyl, di($C_{1-2}$ alkyl)aminosulfonyl, di($C_{1-4}$ alkyl)amino, $C_{1-6}$ carbonylamino, halogen, cyano, nitro, phenyl, benzyloxy and/or by benzylthio, wherein the phenyl groups may themselves be substituted on the phenyl ring by $C_{1-3}$ alkyl, $C_{1-3}$ haloalkyl, $C_{1-3}$ alkoxy, $C_{1-3}$ haloalkoxy, halogen, cyano or by nitro, and wherein the substituents on the nitrogen in the heterocyclic ring are other than halogen;

$D_4$ is oxygen, —O(CO)—, —(CO)O—, —O(CO)O—, —N($C_{1-4}$ alkyl)-O—, —O—N($C_{1-4}$ alkyl)-, sulfur, sulfinyl, sulfonyl, —SO$_2$N($C_{1-4}$ alkyl)-, —N($C_{1-4}$ alkyl)SO$_2$—, —N($C_{1-2}$ alkoxy-$C_{1-2}$ alkyl)SO$_2$— or —N($C_{1-4}$ alkyl)-;

$D_5$ is a $C_{1-6}$ alkylene, $C_{3-6}$ alkenylene or $C_{3-6}$ alkynylene chain, which may be mono- or poly-substituted by halogen or by $D_8$, the unsaturated bonds of the chain not being bonded directly to the substituent $D_4$;

$D_7$ and $D_8$ are each independently of the other hydroxy, $C_{1-6}$ alkoxy, ($C_{3-6}$ cycloalkyl)oxy, $C_{1-6}$ alkoxy-$C_{1-6}$ alkoxy, $C_{1-6}$ alkoxy-$C_{1-6}$ alkoxy-$C_{1-6}$ alkoxy or $C_{1-6}$ alkylsulfonyloxy;

and agronomically acceptable salts/N-oxides/isomers/enantiomers of such compounds.

Alternatively, the triketone may be present in an enolic form and is a compound of formula (ID)

wherein $R^{31}$ and $R^{32}$ are both hydrogen or together form an ethylene bridge.

The compound of formula (ID) wherein both $R^{31}$ and $R^{32}$ are hydrogen is hereinafter referred to as compound (IDa), and the compound of formula (ID) wherein $R^{31}$ and $R^{32}$ together form an ethylene bridge is hereinafter referred to as compound (IDb).

Suitably, the pyrazole is a compound of formula (IE)

(IE)

wherein $R^{33}$, $R^{34}$, $R^{35}$ and $R^{36}$ are each independently selected from hydrogen, halo or $C_{1-4}$ alkyl;

X is —$SO_2$— or —$CH_2CO$—;

j is 2 or 3; and k is zero or 1.

Suitably $R^{33}$, $R^{34}$, $R^{35}$ and $R^{36}$ are each independently hydrogen, chloro or methyl.

Preferred compounds of formula (IE) include 2-[[4-(2,4-dichloro-3-methylbenzoyl)-1,3-dimethyl-1H-pyrazol-5-yl]oxy]-1-(4-methylphenyl)ethanone (benzofenap), (2,4-dichlorophenyl)[1,3-dimethyl-5-[[(4-methylphenyl)sulfonyl]oxy]-1H-pyrazol-4-yl]methanone (pyrazolynate) and 2-[[4-(2,4-dichlorobenzoyl)-1,3-dimethyl-1H-pyrazol-5-yl]oxy]-1-phenylethanone (pyrazoxyfen).

Alternatively, the pyrazole is a compound of formula (IF)

(IF)

wherein $R^{37}$ is $C_{1-2}$ alkyl or chloro; $R^{38}$ is hydrogen or $C_{1-4}$ alkyl; and $R^{39}$ is $C_{1-4}$ alkyl. A preferred compound is [3-(4,5-dihydro-3-isoxazolyl)-2-methyl-4-(methylsulfonyl)phenyl](5-hydroxy-1-methyl-1H-pyrazol-4-yl)methanone.

Benzobicyclon is a compound of formula (IG)

(IG)

Ketospiradox is a compound of formula (IH)

(IH)

In one embodiment of the invention, the HPPD inhibitor is selected from the group consisting of benzobicyclon, benzofenap, isoxaflutole, mesotrione, pyrazolynate and pyrazoxyfen.

In a preferred embodiment, the HPPD inhibitor is mesotrione.

In another embodiment, the HPPD inhibitor is sulcotrione.

In another embodiment, the HPPD inhibitor is tembotrione.

In another embodiment, the HPPD inhibitor is topramesone.

In another embodiment, the HPPD inhibitor is isoxaflutole.

The skilled person will appreciate that the HPPD inhibitors referred to above may exist in enolic tautomeric forms that may give rise to geometric isomers. Furthermore, in certain cases, the various substituents may contribute to optical isomerism and/or stereoisomerism. All such tautomeric forms, racemic mixtures and isomers are included within the scope of the present invention. Furthermore, whilst it is preferred that the HPPD inhibitor is provided in the formulation as its acid form, it may also be provided as agriculturally acceptable salt or chelate. For example, metal chelates of compounds of formula (IB) are described in more detail in EP 0800317. In particular, metal ions which may be useful in forming the metal chelate compounds include di- and tri-valent transition metal ions such as $Cu^{2+}$, $Zn^{2+}$, $Co^{2+}$, $Fe^{2+}$, $Ni^{2+}$ and $Fe^{3+}$. The selection of a particular metal ion to form the metal chelate compound will depend upon the dione compound to be chelated. Those skilled in the art will readily be able to determine the appropriate metal ion for use with a specific dione compound, without undue experimentation. The preferred metal ions are divalent metal ions, particularly $Cu^{2+}$, $Zn^{2+}$, $Co^{2+}$, with $Cu^{2-}$ being especially preferred. The particle size of the HPPD inhibitor can also be reduced by milling if required.

The encapsulated herbicide can be a chloroacetamide herbicide or an isoxazoline herbicide. For the avoidance of doubt it should be understood that both a chloroacetamide and an isoxazoline may be present in the present invention—and that the herbicide may be present as an agrochemically acceptable salt. In a preferred embodiment the encapsulated herbicide is a chloroacetamide. Numerous isoxazoline herbicides are known in the art. In a preferred embodiment the isoxazoline herbicide is selected from the group consisting of 4-[5,5-dimethyl-4,5-dihydro-isoxazole-3-sulfonyl]-difluoro-methyl]-2,5-dimethyl-2H-[1,2,3]triazole, 4-[5,5-dimethyl-4,5-dihydro-isoxazole-3-sulfonyl]-difluoro-methyl]-2-methyl-5-trifluoromethyl-2H-[1,2,3]triazole, 4-[5,5-dimethyl-4,5-dihydro-isoxazole-3-sulfonyl]-difluoro-methyl]-2-ethyl-5-trifluoromethyl-2H[1,2,3]triazole and 3-[[[5-(difluoromethoxy)-1-methyl-3-(trifluoromethyl)-1H-pyrazol-4-yl]methyl]-sulfonyl]-4,5-dihydro-5,5-dimethyl-isoxazole.

Numerous chloroacetamide herbicides are known in the art. Preferably, the chloroacetamide is selected from the group consisting of acetochlor, alachlor, butachlor, dimethachlor, dimethenamid, metazachlor, metolachlor, S-metolachlor, pethoxamid, pretilachlor, propachlor and thenylchlor. It is preferred that the chloroacetamide is selected from the group consisting of acetochlor, alachlor, metolachlor and S-metolachlor. Most preferred is S-metolachlor.

In the formulation of the present invention the chloroacetamide or isoxazoline component is encapsulated and provided as a microcapsule suspension in the aqueous phase. By encapsulated it is meant that the chloroacetamide oil droplets are contained within a discreet barrier of polyurea which acts as a diffusion barrier. This polyurea wall is an asymmetrical membrane formed through in situ polymerization in which the chloroacetamide is able to diffuse through when applied in the field. This membrane is highly cross-linked by the ratio of the monomers used to form it as well as the temperature of reaction used. This is to control the diffusion of the chloroacetamide across it. The polyurea wall provides physical stability as well as a chemical balance of the chloroacetamide and HPPD inhibitor components in the formulation.

Methods for encapsulating chloroacetamide herbicides in such a manner are well reported in the art—see for example U.S. Pat. Nos. 4,280,833, 4,417,916, 4,534,783, 4,563,212 and 4,640,709—and thus well known to the skilled person.

In a preferred embodiment chloroacetamide microcapsules are produced in the following manner. An aqueous solution comprising appropriate emulsifiers and a polyamine is provided in a suitable vessel and stirred at a low speed. Preferred emulsifers are lignosulfonate salts, especially sodium lignosulfonate. In a separate vessel the organic phase is prepared—which comprises combining the chloroacetanilide herbicide and an appropriate polyisocyanate. Preferred isocyanates are blend of toluylene diisocyanate (TDI) and diphenylmethane-4,4'-diisocyanate (MDI)—wherein the mixture of MDI:TDI is approx 3:1. The organic phase is then combined with the aqueous phase with continuous mixing. The particle size of the microcapsules can range from about 1 micron up to about 100 microns in diameter. A particle size range from about 7 to about 12 is preferred. A high shear blade can be used to achieve the desired particle size. Once the desired particle size is obtained the microcapsules are formed by appropriate heating of the mixture for an appropriate time. Typically, heating the mixture to 65-75° C. for approximately 3 hours will suffice. It should be appreciated that the ratio of diisocyanates and the polymerisation temperature should be selected so as to increase the polymer cross linking in order to form a tight capsule around the chloroacetamide and thus minimise the interaction of the chloroacetamide with the HPPD inhibitor in the final formulation.

Glyphosate is a non-selective herbicide available inter alia under the trade name Touchdown®. Glyphosate is suitably in the form of a salt. A wide variety of glyphosate salts are known, including sodium, potassium, ammonium, and various amines, such as the isopropylamine, ethanolamine, diethanolamine and triethylamine salts. The potassium, ammonium and ethanolamine salts are preferred, particularly preferred is the potassium salt as this depresses the solubility of the HPPD inhibitor in the formulation and thus reduces the decomposition of the HPPD inhibitor.

Glufosinate is a non-selective herbicide available under the trade name Liberty®. Glufosinate is suitably in the form of a salt—typically the ammonium salt.

Thus, in a preferred embodiment of the present invention component (d) of the formulation is glyphosate—in particular potassium glyphosate.

It should be appreciated that the use of high electrolyte concentration minimises the decomposition of the HPPD inhibitor in the in aqueous phase. Also, the high electrolyte environment helps keep the chloroacetamide from partitioning into the water phase and thus prevents the HPPD inhibitor from decomposing as a result of it migrating into the chloroacetamide phase.

The herbicide formulation of the present invention may further comprise—or be tank mixed with—one or more additional pesticides, in particular one or more additional herbicides. In a preferred embodiment the one or more additional herbicides is selected from the group consisting of bentazon, metribuzin, bromoxynil, atrazine and terbuthylazine. Furthermore, the pesticides comprised in the formulation of the present invention may also be used in combination with one or more safeners. It is understood that the safener can be included in any one of the phases of the formulation of the present invention—depending on the physical and chemical nature of the safener being considered. Accordingly, the formulation may further comprise a safener selected from the group consisting of AD 67 (MON 4660), benoxacor, cloquintocet-mexyl, cyprosulfamide (CAS RN 221667-31-8), dichlormid, fenchlorazole-ethyl, fenclorim, fluxofenim, furilazole and the corresponding R isomer, isoxadifen-ethyl, mefenpyr-diethyl, oxabetrinil, and N-isopropyl-4-(2-methoxy-benzoylsulfamoyl)-benzamide (CAS RN 221668-34-4).

The safeners may also be in the form of esters or salts, as mentioned e.g. in The Pesticide Manual, 14$^{th}$ Edition (BCPC), 2006. The reference to cloquintocet-mexyl also applies to a lithium, sodium, potassium, calcium, magnesium, aluminium, iron, ammonium, quaternary ammonium, sulfonium or phosphonium salt thereof as disclosed in WO 02/34048, and the reference to fenchlorazole-ethyl also applies to fenchlorazole.

In a preferred embodiment of the pH of the herbicide composition of the present invention is from about 3 to about 7, more preferably from about to about 4 to about 5. Accordingly, the herbicide formulation may further comprise a pH adjuster. The skilled person is well aware of suitable pH adjusters, for example sulphuric acid. However, it is preferred that the pH adjuster is phosphoric acid or especially toluene sulfonic acid (TSA) as it has been shown that these provide extremely good chemical stability of the HPPD inhibitor in the formulation.

The herbicide formulation of the present invention may also include one or more additives to improve the biological performance of the composition, for example by improving wetting, retention or distribution on surfaces; resistance to rain on treated surfaces; or uptake or mobility of a compound. Such additives include surface active agents (SFAs), spray additives based on oils, for example certain mineral oils or natural plant oils (such as soy bean and rape seed oil), and blends of these with other bio-enhancing adjuvants.

In the herbicide formulation concentrate of the present invention it is preferred that SFAs are present at less than 1%—as greater concentrations can lead to physical instability of the concentrate formulation.

Wetting agents, dispersing agents and emulsifying agents may be SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

The present invention further provides a process for the preparation of a herbicide formulation concentrate of the invention, said process comprising the steps of:
(a) separately preparing an (i) HPPD inhibitor mill base, (ii) a chloroacetamide or an isoxazoline herbicide capsule suspension and (iii) a glyphosate and/or glufosinate soluble concentrate
(b) combining components (i), (ii) and (iii) above whilst mixing;
(c) adding a structuring agent whilst still mixing; and
(d) optionally adjusting the pH to from about 3 to about 7.

Before use, the concentrate formulation of the present invention is suitably first diluted, preferably with water, by between 2 and 500 times.

The herbicide formulation of the present invention can thus be used to control plants. 'Control' means kill, reduce or retard growth or prevent or reduce germination. Generally the plants to be controlled are unwanted plants (weeds).

The invention also relates to a method of controlling plants which comprises applying to the plants or to the locus thereof an herbicide formulation according to the present invention.

'Locus' means the area in which the plants are growing or will grow.

The invention also relates to a method of inhibiting plant growth which comprises applying to the plants or to the locus thereof herbicide formulation according to the present invention.

The invention also relates to a method for the selective control of unwanted plants in areas where crops or other useful plants are growing or will grow which comprises applying to the area an herbicide formulation according to the present invention.

The rates of application of compounds contained in the herbicide formulation vary within wide limits and depend on the nature of the soil, the method of application (pre- or post-emergence; seed dressing; application to the seed furrow; no tillage application etc.), the crop plant, the grass or weed to be controlled, the prevailing climatic conditions, and other factors governed by the method of application, the time of application and the target crop.

The application is generally made by spraying the composition, typically by tractor mounted sprayer for large areas, but other methods such as dusting (for powders), drip or drench can also be used.

Useful plants in which the composition according to the invention can be used include crops such as cereals, for example barley and wheat, cotton, oilseed rape, maize, rice, soybeans, sugar beet and sugar cane.

Crop plants can also include trees, such as fruit trees, palm trees, coconut trees or other nuts, vines such as grapes, fruit bushes, fruit plants and vegetables.

Crops are to be understood as also including those crops which have been rendered tolerant to herbicides or classes of herbicides (e.g. ALS-, GS-, EPSPS-, PPO-, ACCase and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®. Especially preferred is maize which has been rendered tolerant to glyphosate and or glufosinate.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesise such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTN33B® (cotton), Bollgard® (cotton), NewLeaf® (potatoes), NatureGard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood to include those which are obtained by conventional methods of breeding or genetic engineering and contain so-called output traits (e.g. improved storage stability, higher nutritional value and improved flavour).

Other useful plants include turf grass for example in golf-courses, lawns, parks and roadsides, or grown commercially for sod, and ornamental plants such as flowers or bushes.

The compositions can be used to control unwanted plants including grasses (collectively, 'weeds'). The weeds to be controlled may be both monocotyledonous species, for example *Agrostis, Alopecurus, Avena, Bromus, Cyperus, Digitaria, Echinochloa, Lolium, Monochoria, Rottboellia, Sagittaria, Scirpus, Setaria, Sida* and *Sorghum*, and dicotyledonous species, for example *Abutilon, Amaranthus, Chenopodium, Chrysanthemum, Galium, Ipomoea, Nasturtium, Sinapis, Solanum, Stellaria, Veronica, Viola* and *Xanthium*. Weeds can also include plants which may be considered crop plants but which are growing outside a crop area ('escapes'), or which grow from seed left over from a previous planting of a different crop ('volunteers'). Such volunteers or escapes may be tolerant to certain other herbicides.

EXAMPLES

Example 1

Making the Chloroacetamide Capsule Suspension (CS)

An aqueous solution was prepared, comprising 2.1 grams Toximul 3465F and 7.8 grams of Reax 105M with 332.6 grams of water.

In a separate vessel 445.5 grams of S-metolachlor (chloroacetamide) is combined with 26.5 grams of Rubinate M and 8.8 grams of Luprinate T80 and blended together uniformly.

The latter organic solution is then added to the aqueous solution and an emulsion is formed by the use of a high shear stirrer. The dispersed organic phase dispersed into droplets that range from 3 to 40 microns in size. This emulsion is then heated to 70° C. and held for 4 hours to allow for the formation of microcapsules. Following the completion of reaction the solution is then cooled to room temperature and under high shear agitation 1 gram of Kelzan S is added and stirred for 20 minutes. Then 0.7 grams of Proxel GXL is added to finish the formulation.

Example 2

Making the Mesotrione Millbase

An aqueous solution was prepared with 64.6 grams of Morwet D-425 and 137 grams of water. To this was added 298.3 grams of mesotrione and the resulting solution was then milled in an attritor media mill to a fine particle size.

Example 3

Making the Structuring System

The suspension system is prepared by shearing 2 grams of Rhodopol 23 in 96 grams of water. After shearing 2 grams of Proxel GXL are added as a bactericide.

Example 4

Making the Final Formulation

The final formulation is prepared by 134.4 grams of the S-metolachlor CS with 22.9 grams of water and under agitation adding 15.2 grams of the mesotrione millbase. This is followed by the addition of 152.7 grams of the Potassium Glyphosate concentrate and then 17.5 grams of the Rhodopol 23 pregel of the previous example. The final pH is then adjusted with 7.4 grams of toluene sulfonic acid to a pH of about 4.2.

Example 5

Comparative HPPD Stability Data—(Toluene Sulfonic Acid (TSA) v. Phosphoric Acid and Gluconic Acid)

The following table demonstrates the difference in stability of the mesotrione when acidified by various acids. This data demonstrates the advantage of using TSA in the formulation of the present invention versus other acids.

|  |  | Percentage Decomposition of Mesotrione | | | |
|---|---|---|---|---|---|
|  |  | Toluene-sulfonic acid | Gluconic acid | Phosphoric acid | No acid |
| 50 C. | 3 DAYS | 2.11% | 3.26% | 1.77% | 11.30% |
|  | 1 WEEK | 2.32% | 5.91% | 2.93% | 20.39% |
|  | 2 WEEKS | 5.94% | 11.61% | 7.09% | 35.25% |
|  | 3 WEEKS | 9.69% | 17.40% | 10.85% | 46.31% |
|  | 1 MONTH | 13.91% | 26.24% | 16.79% | 53.82% |
|  | 2 MONTHS | 28.00% | 54.80% | 36.38% | 77.94% |
|  | 3 MONTHS | 44.55% | 73.08% | 58.11% | 88.38% |
| 45 C. | 1 WEEK | 1.64% | 1.75% | 1.87% | 11.97% |
|  | 2 WEEKS | 3.06% | 4.91% | 2.43% | 19.71% |
|  | 3 WEEKS | 4.12% | 6.77% | 3.13% | 25.71% |
|  | 1 MONTH | 5.85% | 10.22% | 7.12% | 32.01% |
|  | 2 MONTHS | 11.08% | 23.39% | 14.59% | 49.76% |
|  | 3 MONTHS | 18.29% | 35.81% | 23.48% | 62.57% |
| 38 C. | 1 WEEK | 0.75% | 1.59% | 1.30% | 4.63% |
|  | 2 WEEKS | 0.78% | 1.77% | 1.09% | 9.97% |
|  | 3 WEEKS | 1.74% | 3.00% | 1.40% | 13.05% |
|  | 1 MONTH | 2.81% | 4.30% | 3.48% | 17.27% |
|  | 2 MONTHS | 4.00% | 7.42% | 5.08% | 25.52% |
|  | 3 MONTHS | 2.14% | 11.23% | 7.65% | 31.02% |
| −18 C. | 6 MONTHS | 0.05% | −0.18% | 0.94% | 1.07% |

Example 6

Figure 1:
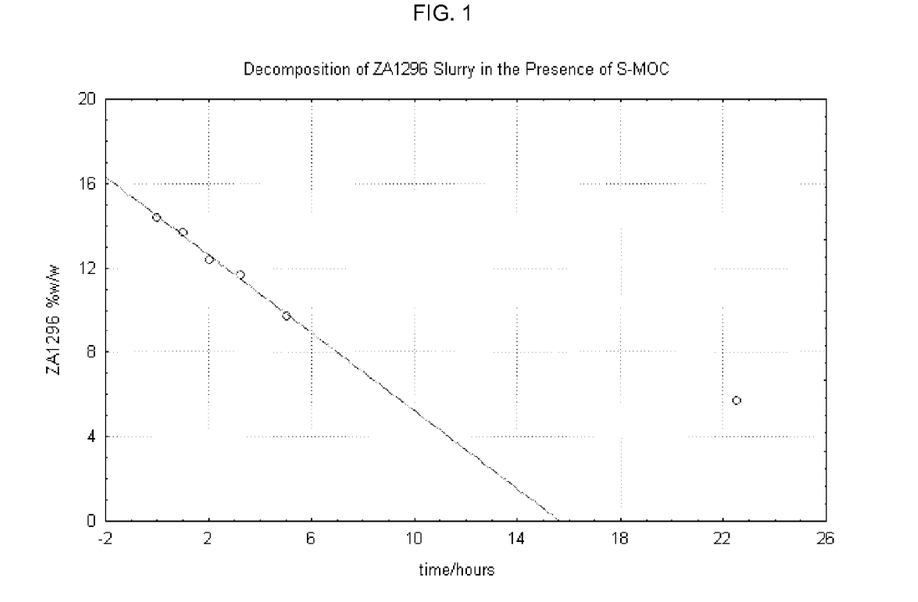
FIG. 1 is a graph illustrating results of Example 6.
Figure 2:
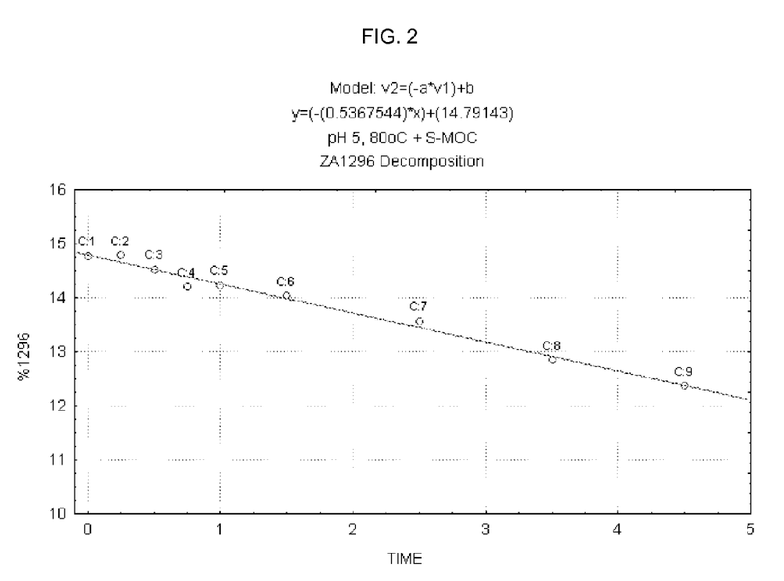
FIG. 2 is a graph illustrating results of Example 6.

Experiments were conducted to look at the stability of mesotrione in chloroacetamides. FIG. 1 and FIG. 2 demonstrate the lack of stability that that the formulation of the present invention overcomes (ZA1296=mesotrione, S-MOC=S-metolachlor).

The invention claimed is:
1. An herbicide formulation comprising:
   (a) an aqueous phase;
   (b) an 4-hydroxyphenylpyruvate dioxygenase (HPPD) inhibitor in suspension in the aqueous phase, wherein the 4-hydroxyphenylpyruvate dioxygenase (HPPD) inhibitor is a triketone;
   (c) an encapsulated chloroacetamide and/or an isoxazoline herbicide in suspension in the aqueous phase;
   (d) glyphosate and/or glufosinate, or an agrochemically acceptable salt thereof, in solution in the aqueous phase; and
   (e) toluene sulfonic acid.
2. An herbicide formulation according to claim 1, which is a pre-mix concentrate comprising:
   (a) an aqueous phase;
   (b) 10-600 g/l HPPD inhibitor in suspension in the aqueous phase;

(c) 10-6000 g/l chloroacetamide and/or an isoxazoline herbicide which is encapsulated and in suspension in the aqueous phase;

(d) 10-3000 g/l glyphosate and/or glufosinate, or an agrochemically acceptable salt thereof, in solution in the aqueous phase; and (e) a structuring agent; and (f) toluene sulfonic acid.

3. An herbicide formulation according to claim 1, wherein the triketone is mesotrione or tembotrione.

4. An herbicide formulation according to claim 1, wherein the chloroacetamide is present and is selected from the group consisting of alachlor, acetochlor, dimethenamid, metolachlor and S-metolachlor.

5. An herbicide formulation according to claim 4, wherein the chloroacetamide is S-metolachlor.

6. An herbicide formulation according to claim 1, wherein component (d) is potassium glyphosate.

7. A process for the preparation of an herbicide formulation according to claim 2, said process comprising the steps of:

(a) separately preparing (i) an HPPD inhibitor mill base, (ii) a chloroacetamide or an isoxazoline herbicide capsule suspension and (iii) a glyphosate and/or glufosinate soluble concentrate;

(b) combining components (i), (ii) and (iii) above whilst mixing;

(c) adding a structuring agent whilst still mixing; and (d) optionally adjusting the pH to from about 3 to 7.

8. A process for the control of unwanted vegetation, said process comprising the application of a herbicidally effective amount of a herbicide formulation according to claim 1 to a locus of the unwanted vegetation.

9. An herbicide formulation according to claim 1, wherein the triketone is mesotrione.

10. An herbicide formulation according to claim 9, wherein the chloroacetamide is present and is selected from the group consisting of alachlor, acetochlor, dimethenamid, metolachlor and S-metolachlor.

11. An herbicide formulation according to claim 10, wherein component (d) is potassium glyphosate.

12. An herbicide formulation comprising:

(a) an aqueous phase;

(b) mesotrione;

(c) an encapsulated chloroacetamide in suspension in the aqueous phase, wherein the chloroacetamide is metolachlor, S-metolachlor, or acetochlor;

(d) glyphosate or an agrochemically acceptable salt thereof, in solution in the aqueous phase; and (e) toluene sulfonic acid in an appropriate amount to provide a pH of from about 3 to about 7.

13. An herbicide formulation according to claim 12, wherein the chloroacetamide is S-metolachlor.

14. An herbicide formulation according to claim 13, wherein component (d) is potassium glyphosate.

15. A process for the preparation of an herbicide formulation according to claim 12, said process comprising the steps of:

(a) separately preparing (i) a mesotrione mill base, (ii) an encapsulated chloroacetamide suspension and (iii) a glyphosate soluble concentrate;

(b) combining components (i), (ii) and (iii) above whilst mixing;

(c) adding a structuring agent whilst still mixing; and (d) adjusting the pH to from about 3 to about 7 via the toluene sulfonic acid.

16. A process for the control of unwanted vegetation, said process comprising the application of a herbicidally effective amount of a herbicide formulation according to claim 12 to a locus of the unwanted vegetation.

17. A process for the control of unwanted vegetation, said process comprising the application of a herbicidally effective amount of a herbicide formulation according to claim 13 to a locus of the unwanted vegetation.

18. A process for the control of unwanted vegetation, said process comprising the application of a herbicidally effective amount of a herbicide formulation according to claim 14 to a locus of the unwanted vegetation.

* * * * *